(12) United States Patent
Cappelleri et al.

(10) Patent No.: US 10,709,324 B2
(45) Date of Patent: Jul. 14, 2020

(54) SYSTEMS AND METHODS FOR PERFORMING A SURGICAL PROCEDURE

(71) Applicant: Purdue Research Foundation, West Lafayette, IN (US)

(72) Inventors: David John Cappelleri, West Lafayette, IN (US); Benjamin Varughese Johnson, West Lafayette, IN (US); Brian Anthony Cole, Montclair, NJ (US)

(73) Assignee: Purdue Research Foundation, West Lafayette, IN (US)

( * ) Notice: Subject to any disclaimer, the term of this patent is extended or adjusted under 35 U.S.C. 154(b) by 279 days.

(21) Appl. No.: 15/222,998

(22) Filed: Jul. 29, 2016

(65) Prior Publication Data

US 2017/0027606 A1    Feb. 2, 2017

Related U.S. Application Data

(60) Provisional application No. 62/199,733, filed on Jul. 31, 2015.

(51) Int. Cl.
*A61B 1/313* (2006.01)
*A61B 17/34* (2006.01)
(Continued)

(52) U.S. Cl.
CPC ............. *A61B 1/313* (2013.01); *A61B 1/018* (2013.01); *A61B 17/00234* (2013.01);
(Continued)

(58) Field of Classification Search
CPC ............ A61B 1/00087; A61B 1/00098; A61B 1/00101; A61B 1/00131; A61B 1/00135; A61B 1/0014; A61B 1/00154; A61B 1/0016; A61B 1/005; A61B 1/0051; A61B 1/0052; A61B 1/0053; A61B 1/0055; A61B 1/0056; A61B 1/0057; A61B 1/0058; A61B 1/008; A61B 1/01; A61B 1/018;
(Continued)

(56) References Cited

U.S. PATENT DOCUMENTS

| 2008/0188869 | A1* | 8/2008 | Weitzner | A61B 1/0014 606/130 |
| 2015/0366572 | A1* | 12/2015 | Sholev | A61B 34/71 606/170 |
| 2016/0296246 | A1* | 10/2016 | Schaller | A61B 17/30 |

FOREIGN PATENT DOCUMENTS

WO    WO 2014125498 A2 *   8/2014   ............. A61B 34/71

* cited by examiner

*Primary Examiner* — Ryan N Henderson
(74) *Attorney, Agent, or Firm* — Hartman Global IP Law; Gary M. Hartman; Domenica N. S. Hartman

(57) ABSTRACT

Systems and methods for performing a surgical procedure within a body cavity. The systems include a cannula having a tubular body with ports located at first and second ends thereof, wherein the second end is configured to be inserted into the cavity. The systems further include one or more tools configured to be inserted into the cannula through the ports on the first end, extend through the body of the cannula, and protrude from the ports on the second end. The tools each include a shaft with a working element on a distal end of the shaft, at least portions of which are capable of articulation relative to the shaft, rotation relative to the cannula, and are configured to perform tasks in the cavity. The working element may be produced with an additive manufacturing technique.

15 Claims, 9 Drawing Sheets

(51) Int. Cl.
    *A61B 17/00*     (2006.01)
    *A61B 34/00*     (2016.01)
    *A61B 1/018*     (2006.01)
    *A61B 17/28*     (2006.01)
    *A61B 17/29*     (2006.01)
    *A61B 1/12*     (2006.01)
    *B33Y 10/00*     (2015.01)
    *B33Y 80/00*     (2015.01)

(52) U.S. Cl.
    CPC .............. *A61B 17/28* (2013.01); *A61B 17/29* (2013.01); *A61B 17/3421* (2013.01); *A61B 17/3423* (2013.01); *A61B 34/71* (2016.02); *A61B 1/126* (2013.01); *A61B 2017/003* (2013.01); *A61B 2017/00261* (2013.01); *A61B 2017/00526* (2013.01); *A61B 2017/2901* (2013.01); *A61B 2017/2905* (2013.01); *A61B 2017/2908* (2013.01); *A61B 2017/3445* (2013.01); *B33Y 10/00* (2014.12); *B33Y 80/00* (2014.12)

(58) Field of Classification Search
    CPC ..... A61B 1/313; A61B 1/3132; A61B 1/3135; A61B 17/29; A61B 17/28; A61B 2017/29; A61B 2017/28; A61B 2017/00261; A61B 2017/003; A61B 2017/00305; A61B 2017/00314; A61B 2017/00318; A61B 2017/00323; A61B 2017/00327; A61B 2017/0034; A61B 2017/2901; A61B 2017/2905; A61B 2017/2908; A61B 1/00133; A61M 25/0133; A61M 25/0136; A61M 25/0138; A61M 25/0141; A61M 25/0144; A61M 25/0147; A61M 25/0161
    See application file for complete search history.

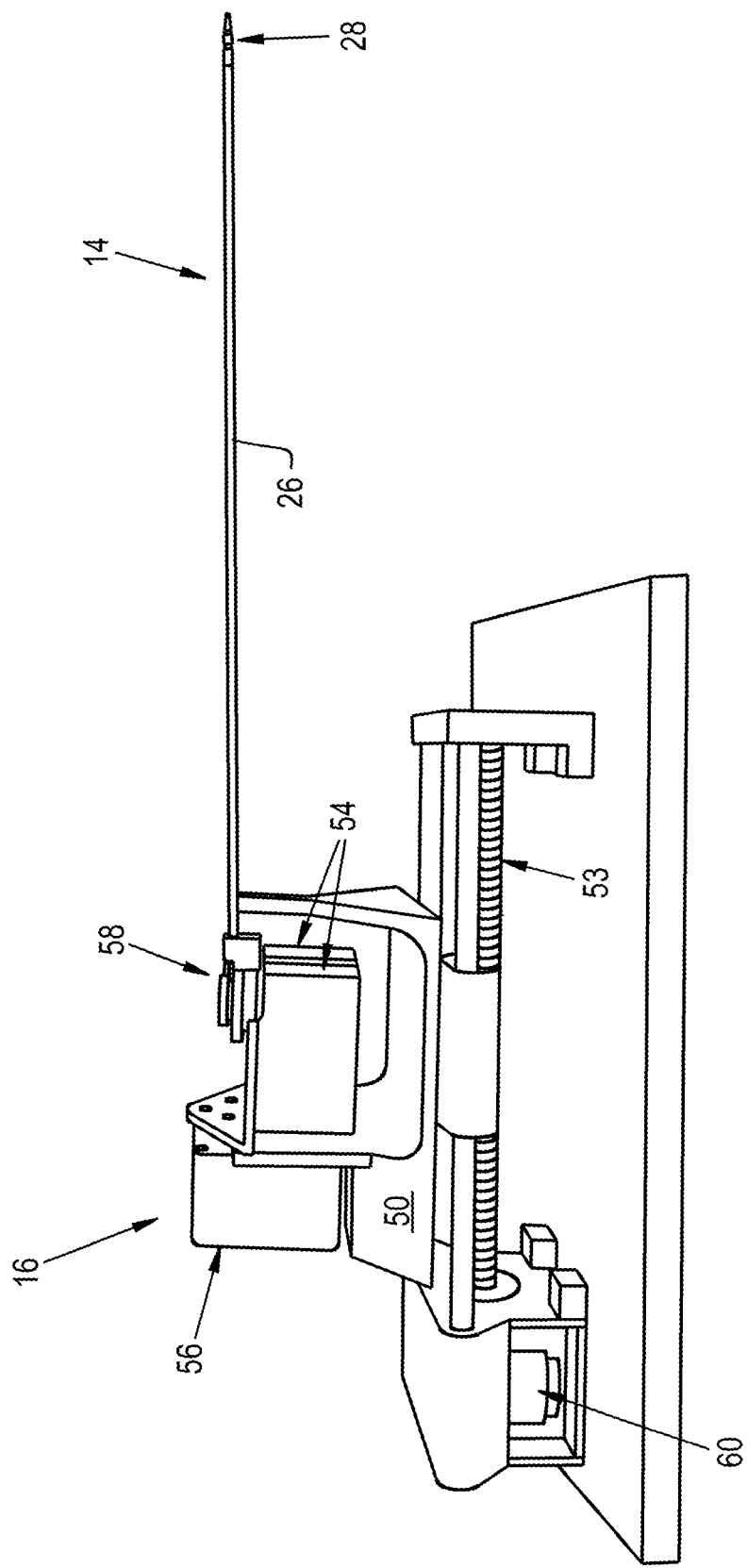

SYSTEMS AND METHODS FOR PERFORMING A SURGICAL PROCEDURE

CROSS REFERENCE TO RELATED APPLICATIONS

This application claims the benefit of U.S. Provisional Application No. 62/199,733, filed Jul. 31, 2015, the contents of which are incorporated herein by reference.

BACKGROUND OF THE INVENTION

The present invention generally relates to tools for working in relatively small working spaces with limited access. The invention particularly relates to instruments for use in minimally invasive surgical procedures.

Pain within a patient's lower back, specifically the lumbar region of the spine, is typically induced by disc herniations or over-compression of the vertebrae. To treat this discomfort, surgeons may perform a microdiscectomy, a minimally invasive (as opposed to open surgery) technique for removing the portion of the herniated disc material that is pressing on the nerve root. While these surgical procedures typically have high success rates and improve patient outcomes relative to more invasive procedures, the tools currently available for performing the procedures have various limitations.

Common instruments available to remove herniated disc material include rigid probes with tips that manipulate and remove the patients' tissue. Nonlimiting examples of such instruments include a set of tools available from Richard Wolf Medical Instruments Corporation under the brand name VERTEBRIS™, a disposable set of tools available from Vertos Medical Inc. under the brand name Mild®, and a single use tool available from Stryker Corporation under the brand name Dekompressor®. Due to the limited working space within the patient, the lack of dexterity of the tools, and occasional limited vision during the procedure, surgeons may be uncomfortable, may be forced to operate blindly for portions of the procedure, and movement of the tools, which are commonly formed of rigid materials, to achieve a necessary orientation can cause inadvertent damage to muscles, soft tissue, and the nerve root.

While most available instruments are rigid, some more recent instruments have been disclosed that are based on a flexible backbone structure to provide improved flexibility. However, such tools generally have a relatively large radius of curvature and hence can be used only in large working spaces. Although surgical tools have been disclosed having diameters less than four millimeters, they are generally expensive to manufacture and require complicated assembly.

Robotic surgical systems are now emerging which are intended to overcome the challenges associated with surgical procedures. However, these systems are generally limited in their practical applications due to their size, capabilities, and cost. Additionally, these systems may require extensive sterilization and draping to reduce the risk of infection.

In view of the above, there is an ongoing desire for devices that are capable of use in surgical procedures, for example, minimally invasive procedures such as microdiscectomy, with improved dexterity and vision relative to currently available instruments.

BRIEF DESCRIPTION OF THE INVENTION

The present invention provides systems and methods for performing surgical procedures with improved dexterity and vision relative to systems and methods performed with currently available instruments.

According to one aspect of the invention, a system for performing a surgical procedure within a cavity of a living body including a cannula having a tubular body with at least first, second, third, and fourth ports located at first and second ends thereof with the second end being configured to be inserted into the cavity, and at least first and second tools each configured to be inserted into the cannula through the first end, extend through the body of the cannula, and protrude from the second end. The first tool enters and exits the cannula through the first and second ports, respectively, and the second tool enters and exits the cannula through the third and fourth ports, respectively. Each of the tools has a shaft with a working element on a distal end of the shaft wherein at least portions of the working element are capable of articulation relative to the shaft, rotation relative to the cannula, and are configured to perform tasks in the cavity.

According to another aspect of the invention, a system for performing a surgical procedure within a cavity of a living body includes a cannula having a tubular body with at least first and second ports located at first and second ends thereof with the second end being configured to be inserted into the cavity, and at least one tool configured to be inserted into the cannula through the first port on the first end, extend through the body of the cannula, and protrude from the second end through a second port. The tool has a shaft with a working element on a distal end of the shaft wherein at least portions of the working element are capable of articulation relative to the shaft, rotation relative to the cannula, and are configured to perform tasks in the cavity. The working element is produced with an additive manufacturing technique that forms components of the working element as a single integral component by fusing particles together.

According to another aspect of the invention, a method of performing a surgical procedure within a cavity of a living body with a system comprising a cannula having a tubular body with at least first and second ports located at first and second ends thereof and at least one tool configured to be inserted into the cannula through the first port on the first end, extend through the body of the cannula, and protrude from the second end through the second port is provided. The method includes producing a working element with an additive manufacturing technique that forms components of the working element as a single integral component by fusing particles together, securing the working element to a distal end of a shaft of the tool, inserting the second end of the tubular body into the cavity of the living body, articulating the working element relative to the shaft within the cavity of the living body, rotating the working element relative to the cannula within the cavity of the living body, and performing at least one task of the surgical procedure with the working element within the cavity of the living body.

Technical effects of the systems and methods described above preferably include the ability to perform tasks of a surgical procedure in a cavity of a living body with improved dexterity and vision relative to currently available instruments.

Other aspects and advantages of this invention will be better appreciated from the following detailed description.

BRIEF DESCRIPTION OF THE DRAWINGS

FIG. 8 shows a tool coupled to an actuator unit in accordance with a nonlimiting embodiment of this invention.

DETAILED DESCRIPTION OF THE INVENTION

Figure 1:
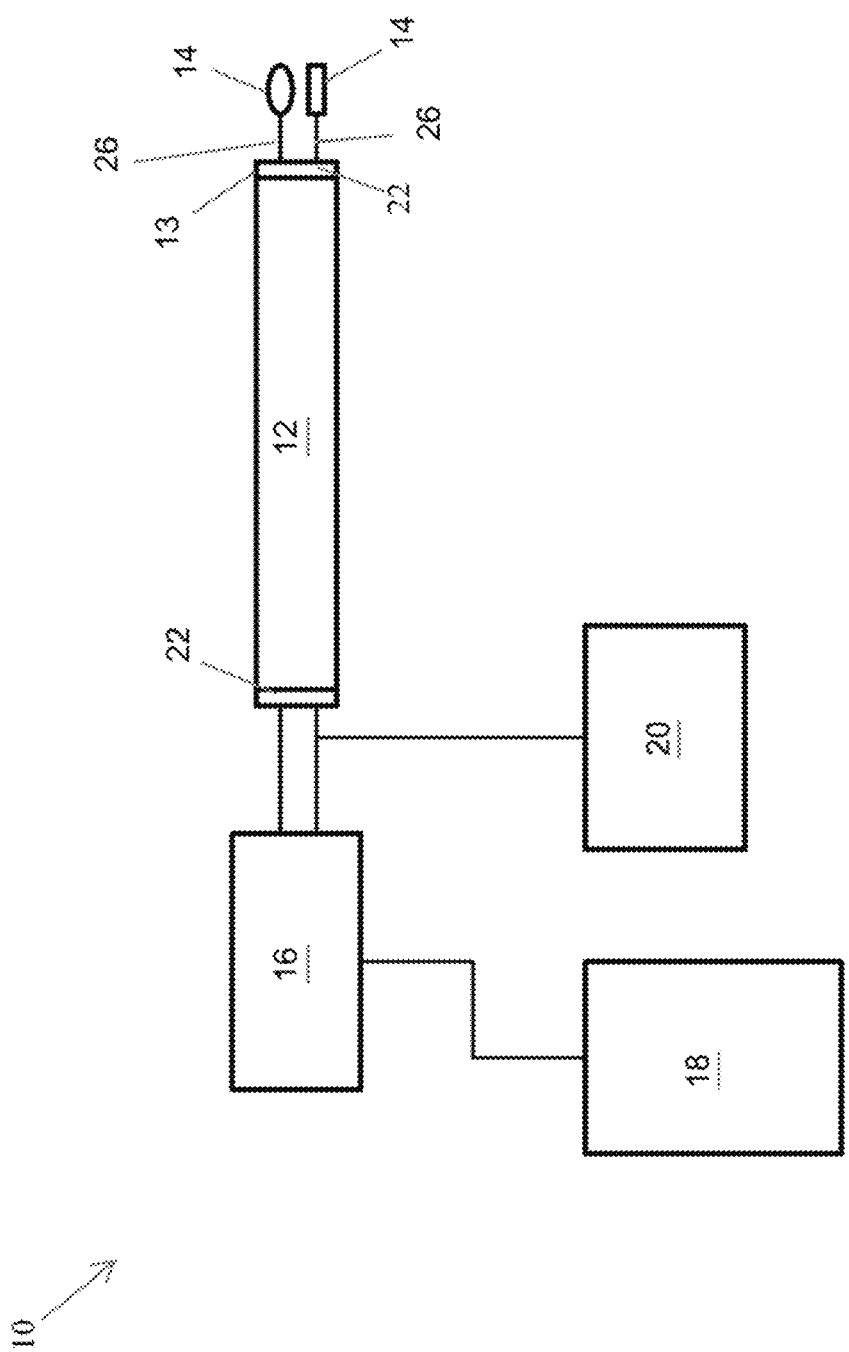
FIG. 1 schematically represents a system comprising tools for performing tasks in an enclosed space in accordance with a nonlimiting embodiment of this invention.

FIG. 1 schematically represents a system 10 configured to perform tasks in a confined working space or enclosed cavity. Although the system 10 will be described below as being used to perform tasks associated with or required by a surgical procedure within a cavity of a living body, such as but not limited to a microdiscectomy performed in a human being, it is within the scope of the invention that the system 10 could be configured for use in any type of confined working space. For example, the system 10 may be configured for use in a surgical procedure or other invasive procedures performed on animals, or may be used in a non-medical field to repair or otherwise access and manipulate objects in difficult to access locations. It is within the scope of the invention that the confined working space or enclosed cavity in which the system 10 is configured to perform tasks may be relatively small, for example, having a volume of about ten cubic centimeters or less, and as small as about three cubic centimeters or less.

Figure 2:
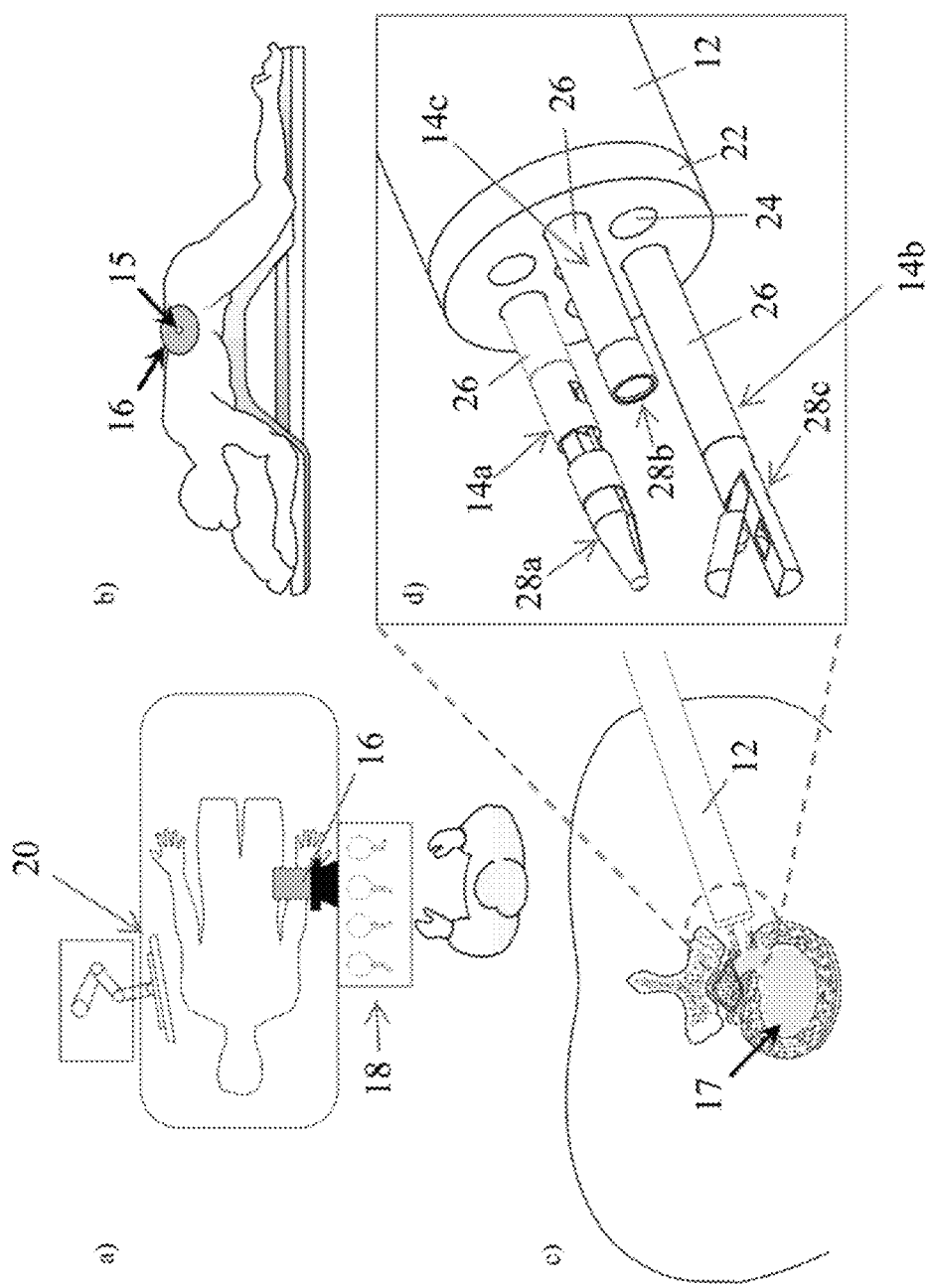
FIG. 2 includes images (a, b, c, and d which schematically represent use of the system of FIG. 1 during a microdiscectomy in accordance with a nonlimiting embodiment of this invention.

The system 10 includes a cannula 12 having a distal end 13 for insertion into a patient during the procedure. Although the body of the cannula 12 could have any shape, it is represented in the drawings as having an elongated tubular body. The cannula 12 is configured to allow one or more surgical tools 14 to be routed therethrough and protrude from the distal end 13 during the procedure. Images (a) through (c) of FIG. 2 schematically represent a nonlimiting embodiment of the system 10 as configured for performing a microdiscectomy. Image (a) represents a surgeon positioned adjacent an operating table on which a patient lies. A control system 18 may be used to enable the surgeon to operating the system 10 using manual controls that provide control of the cannula 12 and the working elements 28, for example, a set of joysticks, or a computer system having software instructions thereon for implementing the surgical procedure. The system 10 may have means for selectively locking the position of an individual working element 28, for example, so that the surgeon can operate the other working elements 28 efficiently. A monitor 20 on an opposite side of the operating table may provide the surgeon with a view of a video captured by a camera within the incision. During the procedure, the distal end 13 of the cannula 12 may be inserted into the patient through an incision 15 to interact with herniated disk material 17.

FIGS. 2 (image d) and 3 schematically represent the distal end 13 as including an adapter 22 comprising several ports 24 from which the tools 14 may protrude. Preferably, the oppositely disposed end of the cannula 12 also includes an adapter 22. The adapter 22 has multiple ports 24 formed therein that provide spacing between and support for the various tools 14, which preferably are capable of being retracted within the cannula 12. Although represented as through-holes having circular cross-sections, the ports 24 may each individually be any shape and/or size to allow passage through and support of a corresponding tool 14. As a nonlimiting example, one or more of the ports 24 may be through-holes having a circular cross-section having a diameter of 0.125 inch (about 3 mm) or more.

FIG. 8 represents the tools 14 as including an elongated sheath 26 having a working element 28 on a distal end thereof. The sheath 26 may be of any diameter (or width) and length, comparable devices being in the nonlimiting ranges of 0.125 inch (about 3 mm) diameter or less and between about 150 and 200 micrometers long. Preferably, the sheath 26 is capable of individually rotating within the cannula 12, and the working elements 28 are capable of articulation relative to the sheath 26. Such functionality provides the ability to change the orientation of the working elements 28 during a surgical procedure without moving the cannula 12, thus reducing damage to tissues surrounding the cannula 12.

Figure 3:
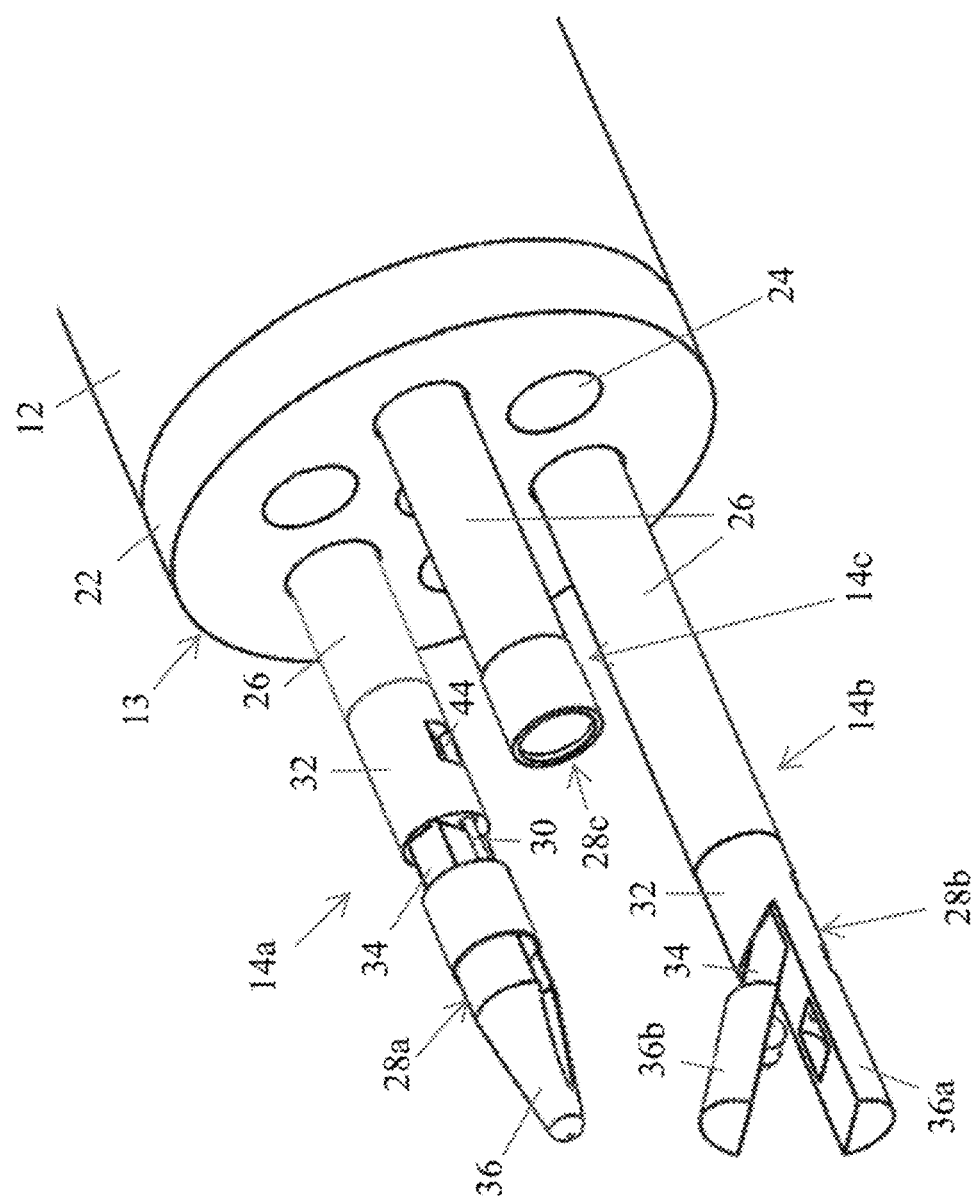
FIG. 3 is an enlarged view of a distal end of the tools of FIG. 2.

As a nonlimiting example, FIG. 3 represents three tools 14a, 14b, and 14c protruding from the distal end 13 of the cannula 12. The tools 14a, 14b, and 14c include working elements 28a, 28b, and 28c on their distal end which are configured to function as a nerve retractor, a grasper, and a camera, respectively. The tool 14a includes a working element 28a having a tip 36 coupled to a base 32 by a flexible joint 34. The base 32 secures the working element 28a to the sheath 26 and may comprise any fastener, threads, or other means for securing the working element 28a to the sheath 26 or may comprise a structure that in conjunction with a fastener is capable of securing the working element 28a to the sheath 26. For example, FIG. 5 represents the working element 28 as comprising a structure 72 for mating with and press-fitting within the sheath 26.

Figure 4:
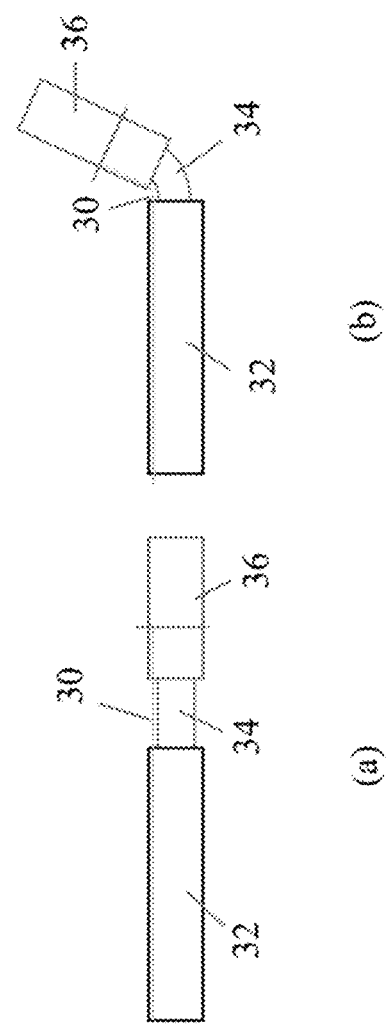
FIG. 4 (images a and b) schematically represents articulation of a working element in accordance with a nonlimiting embodiment of this invention.

The flexible joint 34 allows the tip 36 to be articulated relative to the base 32, as represented in FIG. 4. To facilitate such articulation, at least two guide wires 30 may be coupled to the tip 36 and threaded through the working element 28, into the sheath 26, and through the sheath 26 to an oppositely disposed end of the cannula 12 where the guide wires 30 may be functionally coupled to, for example, an actuator unit 16 (FIGS. 1, 2, and 8). FIG. 8 represents a nonlimiting embodiment of the actuator unit 16 as connected to a single sheath 26. As represented, the actuator unit 16 may comprising servo motors 54 and pulleys 58 for selectively providing or releasing tension on the guide wires 30 to manipulate the working elements 28, an additional servo motor 56 for rotating the sheaths 26, and a platform 50, lead screw 53, and stepper motor 60 for retracting or extending the tools 14. It should be understood that these components may be substituted with other means capable of selectively providing or releasing tension on the guide wires 30 to retract or extend the tools 14, articulate the working elements 28, rotate the working elements 28, or otherwise manipulate the tip 36. Preferably, the working elements 28 have a range of motion of at least 80 degrees of rotation (Yaw).

The tip 36 of the working element 28 may be any device capable of assisting in the performance of the surgical procedure. For example, the tip 36 of the working element 28 may be a surgical manipulator (such as but not limited to a rongeur, an elevator, a hook, a curette, a dissector, a grasper, a scalpel, etc.), a camera, a suction tip of an irrigation system, a drill, or any other device.

Figure 5:
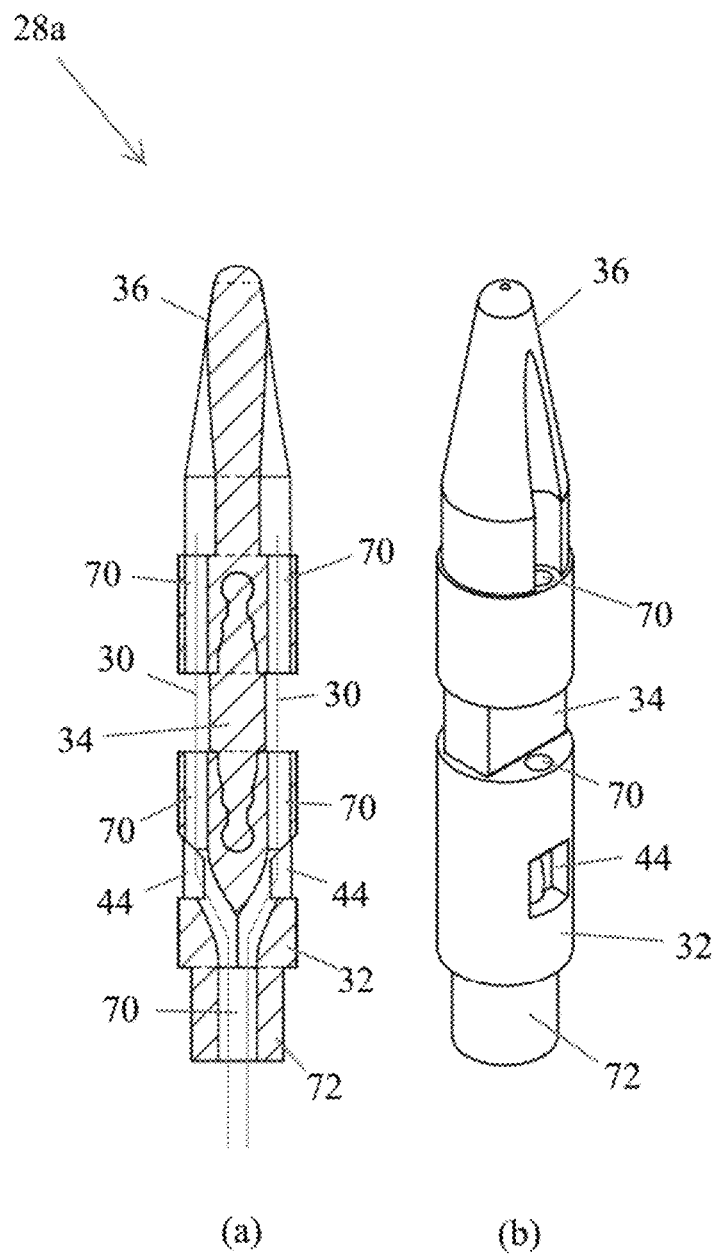
FIG. 5 includes a cross-sectional view (image a) and perspective view (image b) which schematically represent nonlimiting working elements configured as a nerve retractor in accordance with a nonlimiting embodiment of this invention.
Figure 6:
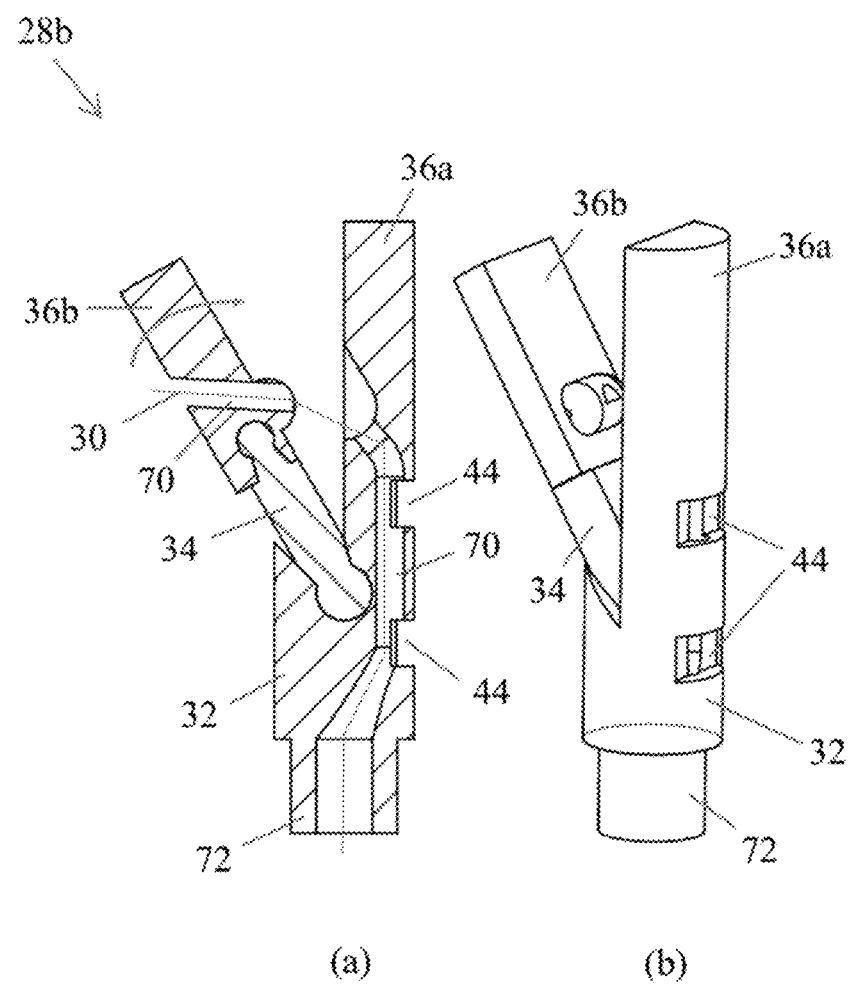
FIG. 6 includes a cross-sectional view (image a) and perspective view (image b) which schematically represent nonlimiting working elements configured as a grasper in accordance with a nonlimiting embodiment of this invention.

FIGS. 5 and 6 schematically represent nonlimiting embodiments of working elements 28a and 28b configured to function as a nerve retractor and a grasper, respectively. Images (a) of FIGS. 5 and 6 are cross sectional views of the working elements 28a and 28b, respectively. Referring to FIG. 5, the working elements 28a includes a tip 36 coupled to a base 32 via a flexible joint 34. As represented, the working element 28a includes passages 70 through which the guide wires 30 may be routed.

Figure 7A:
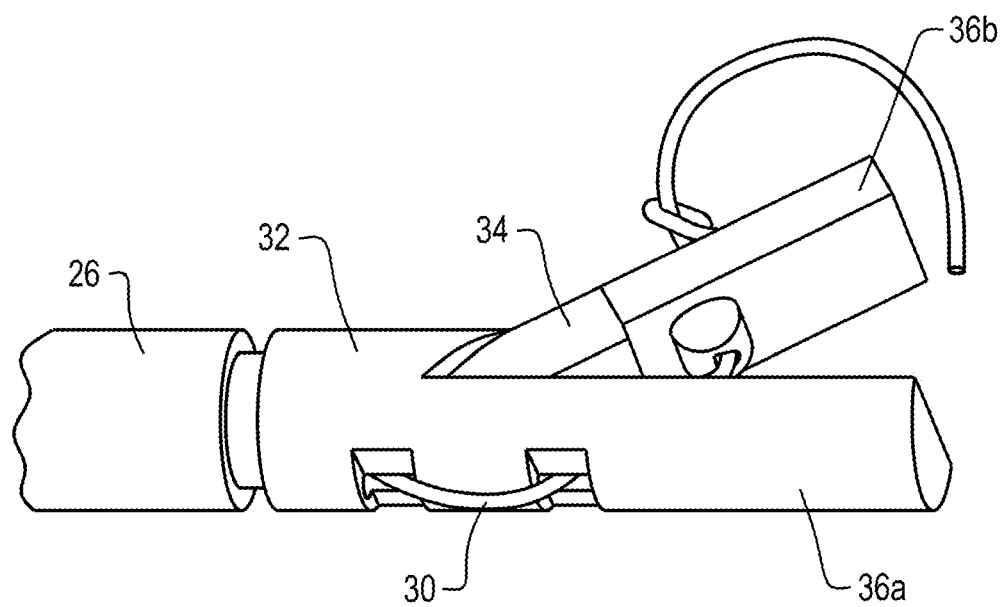
FIG. 7 includes two images that show a grasper type tool in both its open and closed positions.
Figure 7B:
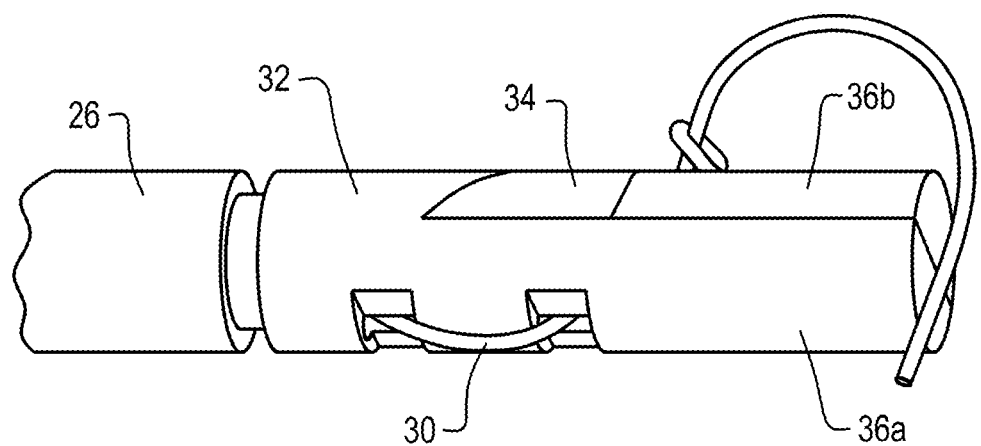

Referring to FIG. 6, the working element 28b includes a first tip 36a directly coupled to a base 32 and fixed in a permanent position relative thereto, and a second tip 36b coupled to the base 32 by a flexible joint 34. The working element 28b also includes passages 70 through which a guide wire 30 may be routed. Manipulation of the guide wire 30 provides for articulation of the second tip 36b relative to the base 32 and the first tip 36a. As such, the working element 28b is capable of providing a gripping functionality by clasping an object between the first and second tips 36a and 36b. FIG. 7 represents the working element 28b in open and closed positions. During the procedure, the nerve retractor (28a) may be used to articulate and retract the nerve such that the grasper (28b) can access the cavity and remove the herniated disk material 17.

The various components of the working element 28 may be formed of any material. Preferably, the base 32 and the tip 36 are formed of materials sufficiently rigid to perform their intended functions, and the joint 34 is sufficiently pliable or flexible such that the working element 28 may articulate. Nonlimiting examples include various polymeric and elastic materials. A specific nonlimiting combination of materials includes a rubber-like polymeric material commercially available under the brand name Tango Black™ for the joint 34 and a rigid polymeric material commercially available under the brand name Vero White™ for the base 32 and tip 36, both materials produced by Stratasys Ltd. Alternatively, the two material may be combined in various ratios individually specific to the base 32, joint 34, and tip 36 which provide a desired stiffness. Preferably, the working elements 28 are relatively small such that they can perform their respective tasks, rotate, and articulate with the confined working space or cavity, including relatively small confined working spaces having a volume of about three centimeters or less.

Although the various components of the working elements 28 could be separately produced and assembled, a preferred, but nonlimiting, aspect of the invention includes producing one or more of the working elements 28 with an additive manufacturing technique, such as but not limited to a three-dimensional printing technique that forms the various components as a single integral component by fusing particles together with, for example, a scanning electron, laser, or ion beam. Since the various components have different functions, it is likely that they may be formed of different materials, combination of materials, or have different ratios of their respective materials. Therefore, the working elements 28 are preferably produced with a multi-material three-dimensional printer. Forming the working elements 28 with such printing techniques may reduce assembly operations during production, reduce the cost of manufacturing, and/or provide individual users of the system 10 with the capability to design and produce custom working elements 28 to suit their individual needs. It is foreseeable that the working elements 28, especially those produced with an additive manufacturing technique, may have a sufficiently low cost such that they may be considered disposable. Therefore, it is within the scope of the invention that the working elements 28 may be removed from the shaft 26 and disposed after performing the procedure, rather than cleaning or sterilizing them for reuse.

Figure 9A:
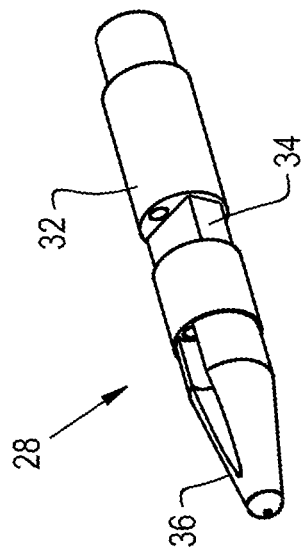
FIGS. 9A, 9B, 9C, and 9D contain four images that depict steps in the production of a working element that was produced with a three dimensional printing process.
Figure 9B:
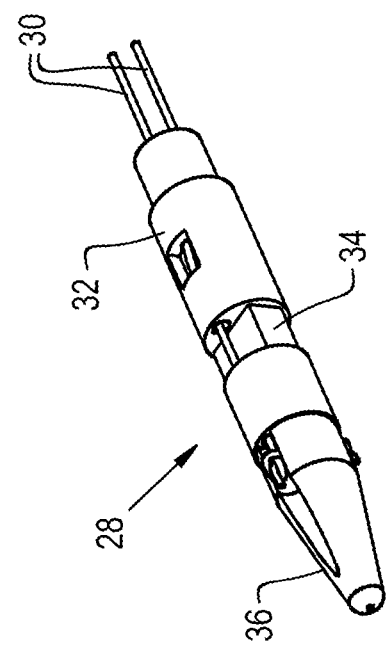
Figure 9C:
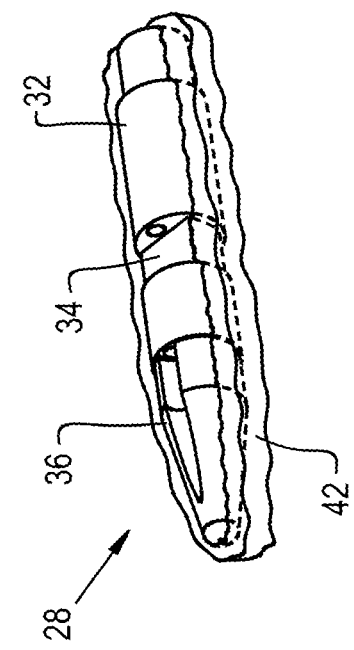
Figure 9D:
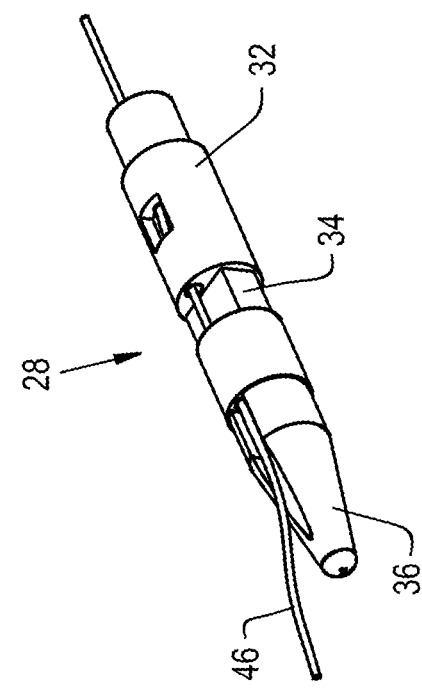

FIGS. 9A, 9B, 9C, and 9D contain four images that sequentially represent steps in production of a working element 28 that was formed using an additive manufacturing technique, specifically a three-dimensional printing technique. The working element 28 was printed using a multi-material printer commercially available from Stratasys Ltd. under the brand name Objet350 Connex3™. After printing, the working element 28 was connected to support materials which were used to support and stabilize the working element 28 during the printing process. FIG. 9A shows the working element 28 encased in an external support material 42, FIG. 9B shows the working element 28 after the external support material 42 has been removed, and FIG. 9C shows a metal wire 46 being used to clear internal support material from passages configured to be used with the guide wires 30. The working element 28 includes ports 44 configured to facilitate removal of the internal support material by reducing the likelihood of clogging within the passages. FIG. 9D shows the final working element 28 with all support material removed and guide wires 30 routed therethrough.

As represented in FIGS. 1, 2 (image a), and 3, the system 10 may include a camera system that includes a tool 14 comprising a camera as the working element 28. The camera may include a light source, or the system 10 may separately include a tool 14 with a light source as the working element 28. For example, the working element 28 may include a base 32, a flexible joint 34, and a tip 36, wherein the tip 36 includes an integrated camera and light source. In such embodiment, the joint 34 preferably allows the camera and light source to be capable of rotation relative to the cannula 12 and articulation relative to the shaft 26. It is also within the scope of the invention that multiple cameras and/or light sources may be used simultaneously with the system 10. Preferably, the camera and light source fit through the ports 24 in the adapter 22 and are capable of retracting into the body of the cannula 12. FIGS. 1 and 2 (image a) represent the system 10 as further including a monitor 20 that may be functionally connected to the camera to provide images and/or video captured by the camera from the inside of the confined working space during the procedure. As nonlimiting examples, the camera and monitor may have wireless communication capabilities or may be coupled with electrical wires routed through the shaft 26 of the tool 14.

The system 10 may include an irrigation system capable of cleaning a lens of the camera, for example, of accumulated fog or blood, or the confined working space in general. Such an irrigation system may include a shaft 26 or tube (not shown) capable of fluidically transporting a cleaning solution and configured to be routed through the cannula 12 and protrude from one of the ports 24 at the distal end 13. Such an irrigation system may be capable of providing a cleaning solution to the lens of the camera and to the confined working space in general. The cleaning solution may be a fluid, which may be a gas, liquid, or gas or liquid solid solution capable of providing the desired cleaning functionality. For surgical procedures performed within a living body, the cleaning solution may be, but is not limited to, a saline solution.

In view of the foregoing, the system 10 provides functionality that may be used in surgical procedures and provides positive aspects of some of the most popular microdiscectomy procedures in aspects such as incision size and manipulation space utilization. Combined with the dexterity the working elements 28, and the feature of coordinated manipulation, the system 10 may significantly aid surgeons in performing surgery and promote improved success rates. This may lead to reduced hospital stays, reduced chances of infection, and quicker recovery for their patients.

As a nonlimiting example, the system 10 may be used, for example, by a surgeon to perform a surgical procedure within a cavity of a living body by inserting the distal end 13 of the body of the cannula 12 into the cavity of the living body, and therein perform various tasks of the surgical procedure with the working elements 28. Such tasks may require or be promoted by articulating the working element 28 relative to the shaft 26 within the cavity, and/or rotating the working element 28 relative to the cannula 12 within the cavity. It is foreseeable that the surgeon may produce one or more of the working elements 28 with an additive manufacturing technique that forms components of the working element as a single integral component by fusing particles together, and then securing the working element to a distal end of a shaft of the tool prior to performing the surgical procedure.

While the invention has been described in terms of specific embodiments, it is apparent that other forms could be adopted by one skilled in the art. For example, the physical configuration of the system 10 and its various components could differ from that shown, and materials and processes/methods other than those noted could be used. Therefore, the scope of the invention is to be limited only by the following claims.

The invention claimed is:

1. A system for performing a surgical procedure within a cavity of a living body, the system comprising:
    a cannula having a tubular body with at least first and second ports located at first and second ends thereof, the second end configured to be inserted into the cavity; and
    at least a first tool configured to be inserted into the cannula through the first port on the first end, extend through the body of the cannula, and protrude from the second end through a second port, the first tool comprising a shaft with a working element on a distal end of the shaft, the working element comprising a base, a flexible joint directly coupled to the base, and at least a first portion coupled to the base by the flexible joint and capable of articulation relative to the base and the shaft and rotation relative to the cannula, the working element being configured to perform tasks in the cavity;
    wherein the working element is produced during an additive manufacturing step so that the base, the flexible joint, and the first portion of the working element are a single integral component as a result of the base, the flexible joint, and the first portion being formed by particles fused together, the flexible joint is formed of a flexible material such that the first portion is able to articulate relative to the base, and the base and the first portion are formed of materials that are different than the flexible material of the flexible joint so that the base and the first portion are more rigid than the flexible material of the joint.

2. The system of claim 1, wherein the flexible material of the flexible joint has a first end embedded in the material of the base and an oppositely-disposed second end embedded in the material of the first portion.

3. The system of claim 1, wherein the tubular body of the cannula further has third and fourth ports located at the first and second ends thereof, the system further comprising a second tool configured to be inserted into the cannula through the first end, extend through the body of the cannula, and protrude from the second end, the first tool entering and exiting the cannula through the first and second ports respectively, the second tool entering and exiting the cannula through the third and fourth ports respectively, the second tool comprising a shaft with a working element on a distal end of the shaft of the second tool that is different and separate from the working element of the first tool, at least a portion of the working element of the second tool being capable of articulation relative to the shaft of the second tool and rotation relative to the cannula, the working element of the second tool being configured to perform tasks in the cavity.

4. The system of claim 1, further comprising a guide wire associated with the first tool, the guide wire being routed through the shaft to the first portion of the working element to articulate the first portion.

5. The system of claim 4, further comprising an actuator unit functionally coupled to the guide wire and operable to selectively apply or release tension on the guide wire to articulate a tip of the working element of the first tool.

6. The system of claim 5, further comprising a control system operable to control the actuator unit.

7. The system of claim 1, further comprising a camera system and an irrigation system, the camera system comprising:
    a shaft with a camera on a distal end of the shaft, the shaft configured to be inserted into the cannula through a third port on the first end, extend through the body of the cannula, and protrude from the second end through a fourth port;
    a light source configured to provide illumination for the camera; and
    a display configured to display images or video captured by the camera;
the irrigation system comprising:
    a shaft configured to be inserted into the cannula through a fifth port on the first end, extend through the body of the cannula, protrude from the second end through a sixth port, and fluidically transport a cleaning solution to a lens of the camera and to the cavity.

8. The system of claim 7, wherein the camera is capable of articulation relative to the shaft of the camera system.

9. The system of claim 3, wherein the working element of the second tool is produced with an additive manufacturing technique that forms components of the working element of the second tool as a single integral component by fusing particles together.

10. The system of claim 1, wherein the first portion defines a tip of the tool, and the working element of the first tool is chosen from the group consisting of a nerve retractor, a surgical manipulator, a camera, a suction tip of an irrigation system, and a drill.

11. The system of claim 1, wherein the working element further comprises a first tip of the first tool fixed in a permanent position relative to the base, the first portion defines a second tip of the tool, the system comprises a guide wire to articulate the first portion relative to the base and the first tip, and the first and second tips define a grasper.

12. The system of claim 3, further comprising a third tool configured to be inserted into the cannula through a fifth port on the first end, extend through the body of the cannula, and protrude from the second end through a sixth port.

13. The system of claim 1, wherein the surgical procedure is a microdiscectomy and the cavity has a volume of three cubic centimeters or less.

14. The system of claim 1, wherein the cavity has a volume of equal to or less than ten cubic centimeters and the working element of the first tool is configured to perform the tasks, articulate, and rotate within the cavity.

15. A method of performing a surgical procedure with the system of claim 1, the method comprising:
    securing the working element to a distal end of a shaft of the first tool;
    inserting the second end of the tubular body into a cavity of a living body;
    articulating the working element relative to the shaft within the cavity of the living body;
    rotating the working element relative to the cannula within the cavity of the living body; and
    performing at least one task of the surgical procedure with the working element within the cavity of the living body.

* * * * *